United States Patent [19]

Purcell

[11] Patent Number: 4,822,351

[45] Date of Patent: Apr. 18, 1989

[54] POWDER SPIKE HOLDER

[75] Inventor: Bradford P. Purcell, Alta Loma, Calif.

[73] Assignee: IMS Limited, South El Monte, Calif.

[21] Appl. No.: 30,441

[22] Filed: Mar. 25, 1987

[51] Int. Cl.[4] .............................................. A61B 19/00

[52] U.S. Cl. .................................... 604/411; 604/414; 141/291

[58] Field of Search ............... 604/414, 416, 411, 405, 604/236, 249, 251-256, 87-89; 141/291, 292, 198-301

[56] References Cited

U.S. PATENT DOCUMENTS

| | | | |
|---|---|---|---|
| 1,139,720 | 5/1915 | Reed | 604/236 |
| 3,159,159 | 12/1964 | Cohen | 604/236 |
| 3,924,741 | 12/1975 | Kachur et al. | 604/416 |
| 3,938,520 | 2/1976 | Scislowicz et al. | 604/414 |
| 4,020,839 | 5/1977 | Klapp | 604/414 |
| 4,610,374 | 9/1986 | Buehler | 604/414 |
| 4,657,534 | 4/1987 | Beck et al. | 604/89 |

*Primary Examiner*—John D. Yasko
*Attorney, Agent, or Firm*—Christie, Parker & Hale

[57] ABSTRACT

The novel combination comprising:

a container having a cylindrical neck of reduced cross-section terminating in an open end, said neck having a projection on its inner surface in proximity to said open end, and a closure for said open end having a skirt portion receivable in said open end and a shoulder at its outer end adapted to move into abutting relationship with the end of said cylindrical neck, said skirt portion having a cut out adapted for receiving said projection on the inner surface of said neck to hold said shoulder in non-abutting relationship with the end of said neck, said closure including a central fluid passage and a transverse fluid passage in communication therewith, the ends of said transverse fluid passage being sealed by the inner surface of said neck when said closure is held in the non-abutting position by the engagement of said projection in said cut out, said engagement being adapted to be overcome by force applied to the end of said closure whereby said shoulder is brought into abutting relationship with the end of said neck and the transverse passage is moved out of said neck and into fluid communication with the interior of said container.

7 Claims, 2 Drawing Sheets

POWDER SPIKE HOLDER

BACKGROUND OF THE INVENTION

Heretofore, various devices for the packaging and dispensing of drugs have been proposed. According to U.S. Pat. No. 3,938,520, there is disclosed a device for transferring a material from a first container to a second container. This device has a container having an opening for storing the material to be transferred, a closure sealing the opening in the container and a transfer member constructed and arranged for opening of the closure to permit transfer of the material from the first container to the second container. The closure includes a diaphragm section sealing the opening in the container with means affixing the closure to the container. Retaining means are provided such that the transfer member has retentive movement toward the sealing diaphragm section of the closure and ready release of the transfer member from the closure. The body of the transfer member includes a piercing end on the end of the body projecting from the closure and a cutting element extending from the end opposite the piercing end of the body and receivable within the closure to open the closure and permit transfer of material between the containers, the cutting element being disposed adjacent the end of the one channel and is adapted to receive the tip of a syringe.

This device involves and requires a number of pieces which much be manufactured and properly assembled. The operation of the device involves the cutting by piercing of a plastic diaphragm. The cutting action is somewhat abrupt. The present invention completely departs from the foregoing arrangement and, it is believed, represents a significant advance in the art of pharmaceutical packaging.

More particularly, according to my invention, the medication is completely sealed at the factory and at all times prior to use. At the point of use, the device is operated by smooth, sliding action to bring the elements into the position for transfer of the packaged medication to another container. The device is simple to make and use, it is smooth in operation, and esthetically attractive.

It is to be expected that the device of this invention will be widely adapted in the art.

SUMMARY OF THE INVENTION

Briefly, the present invention comprises the novel combination comprising:

a container having a cylindrical neck of reduced cross-section terminating in an open end, said neck having a projection on its inner surface in proximity to said open end, and a closure for said open end having a skirt portion receivable in said open end and a shoulder at its outer end adapted to move into abutting relationship with the end of said cylindrical neck, said skirt portion having a cut out adapted for receiving said projection on the inner surface of said neck to hold said shoulder in non-abutting relationship with the end of said neck, said closure including a central fluid passage and a transverse fluid passage in communication therewith, the ends of said transverse fluid passage being sealed by the inner surface of said neck when said closure is held in the non-abutting position by the engagement of said projection in said cut out, said engagement being adapted to be overcome by force applied to the end of said closure whereby said shoulder is brought into abutting relationship with the end of said neck and the transverse passage is moved out of said neck and into fluid communication with the interior of said container.

It is an object of this invention to provide a novel medicament package.

More particularly, it is an object of this invention to provide a new medicament package for dried or lyophilized medication.

In another aspect, it is an object of my invention to provide a simpler and better operating transfer device for transferring medication for a first container to a second container.

These and other objects and advantages of this invention will be apparent from the more detailed description which follows, taken in conjunction with the accompanying drawings.

DESCRIPTION OF PREFERRED EMBODIMENTS

Turning to the drawings.

Figure 1:
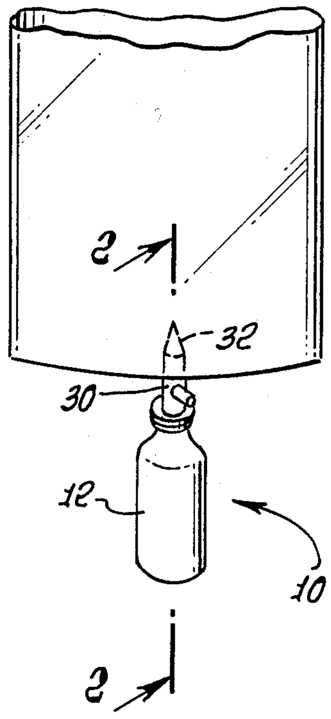
FIG. 1 is a perspective view showing the use of the novel device of this invention.

Turning to the drawings in more detail.

The container 10 is normally a blown plastic "squeeze" bottle having generally cylindrical side walls 12, a closed bottom end (not shown), and a cylindrical neck 14 of reduced cross-section. Molded integrally and slightly recessed within the open end of neck 14 is an annularly projecting ring 16.

The closure, generally 18 has a skirt portion 20 which is snugly receivable within the neck 14 of container 10. The closure 18 has a shoulder 22 at its outer end which, in the "as shipped" or initial position, shown in FIG. 5, is held in a raised, non-abutting position by ring 16 which is engaged in annular groove 24 in skirt position 20.

Figure 2:
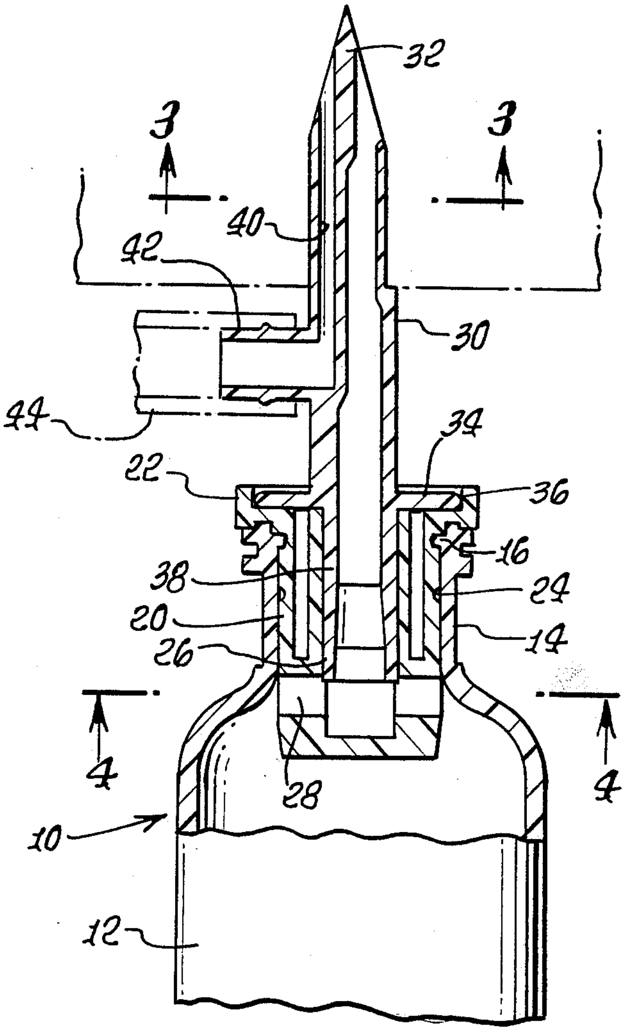
FIG. 2 is a sectional view taken along the line 2—2 in FIG. 1.
Figure 3:
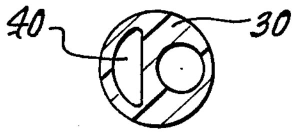
FIG. 3 is a sectional view taken along the line 3—3 in FIG. 2.
Figure 4:
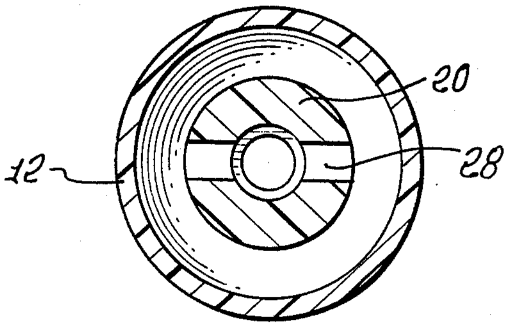
FIG. 4 is a sectional view taken along the line 4—4 in FIG. 2.
Figure 5:
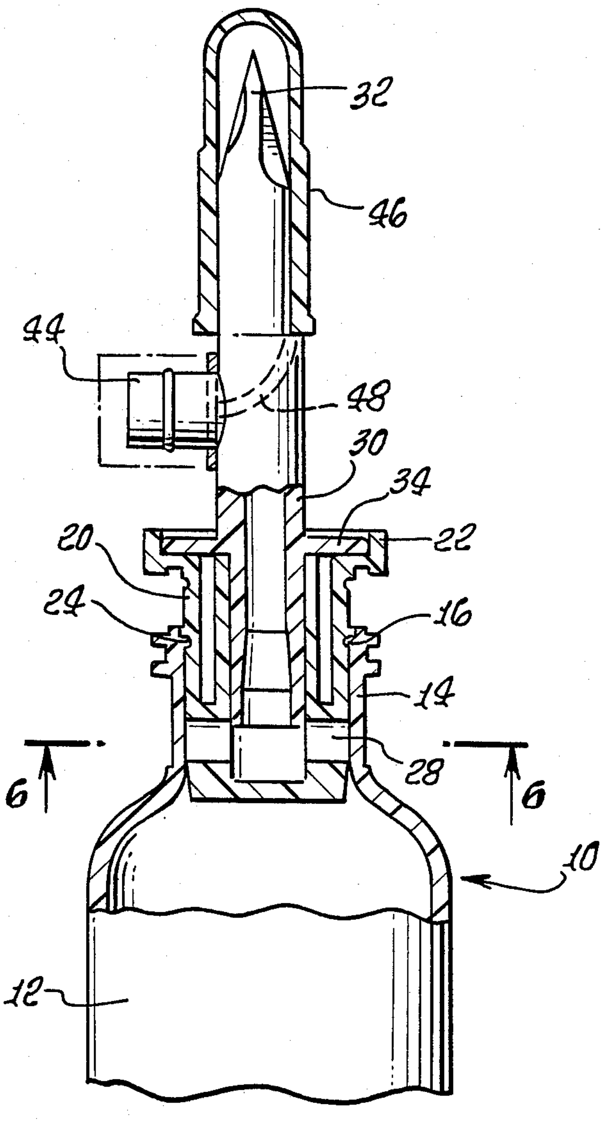
FIG. 5 is a side view of the device of FIGS. 1 to 4, in partial breakaway, the device being in its initial or "as shipped" position.
Figure 6:
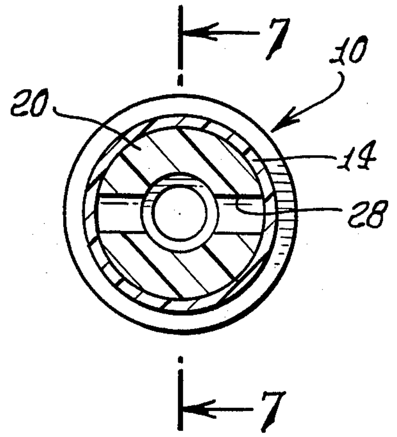
FIG. 6 is a section taken along the line 6—6 in FIG. 5.
Figure 7:
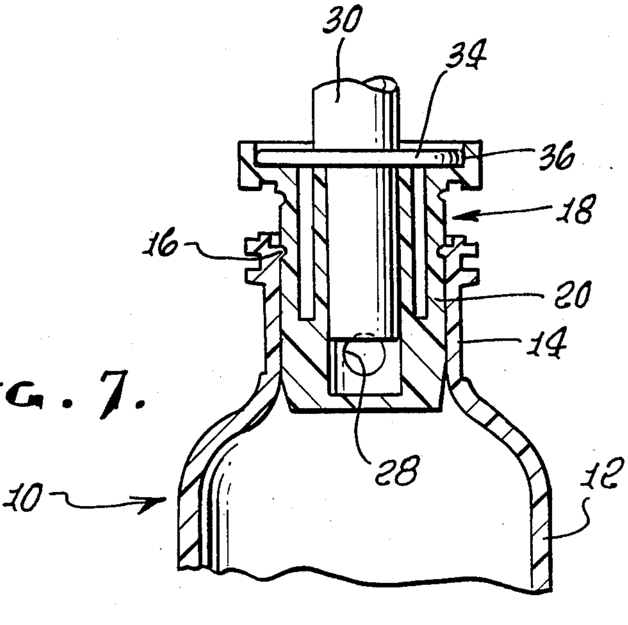
FIG. 7 is a partial section taken along the line 7—7 in FIG. 6.

At the time of use, the closure 18 is manually pushed from the initial position of FIG. 5 to the second operational position of FIG. 2, the manual pressure being sufficient to overcome the resistance to moderate movement and impact provided by the engagement of ring 16 in groove 24. When the closure 18 is in the second position as in FIG. 2, the underside of shoulder 22 normally abuts the open end of neck 14.

The closure 18 has a central longitudinally disposed fluid pathway 26 and a communicating transverse pathway 28, so that when the closure 18 is in the second position of FIG. 2, there is a continuous fluid pathway from the interior of container 10 through closure 18 and the spike 30 to the sharpened end or scarf 32.

In the first position of FIG. 5, the ends of transverse pathway 28 are sealed by the inside walls of cylindrical neck 14. The sealing position of closure 18 are normally of semi-rigid plastic so that a tight seal against the inside walls of cylindrical neck 14 is maintained.

The spike 30 is usually a separate molded piece of rigid plastic. The spike 30 has a disk-like element 34 integrally formed therearound which is tightly received in the recess 36 within the end of closure 18. Also integrally formed with spike 30 is the projection 38 which is received within the longitudinal pathway 26 in closure 18, terminating at transverse pathway 28.

The spike 30 is also provided with an airway 40 terminating in a portion 42 which is at 90° thereto. The portion 42 may hold an air filtration medium (not shown). If so, the medium is held in place by a retainer 44 which is partially shown at 44.

The scarf 32 of spike 30 is covered when not in use by protective cover 46 which is held by a slight interference fit and is manually removable. The protective cover 46 is held to the outside of the airway 42 by a resilient plastic tether 48 or strap so that the cap cannot be lost and is held with the device during use.

In operation, the device is taken as shown in FIG. 5, by manual pressure applied to the closure 18 via shoulder 22, the closure is slid downwardly relative to container 10, to the position shown in FIG. 2. The cap 46 is removed, and the scarf 32 of spike 30 is thus exposed. The entire device is then usually inverted and the spike forced through a rubber-stopper closure on a diluent or intravenous solution bottle or bag (shown only in general outline in the drawings since such bags and bottles are well-known and do not form part of this invention). The assembly is then inverted again as in FIG. 1 and the container 10 is squeezed to pull liquid from the diluent or intravenous solution bag or bottle into container 10, dissolving or suspending the contents thereof, which is normally a powdered or lyophilized medicament such as thiopental sodium. Upon inversion still another time, the liquid bearing the now-dissolved or suspended medicament is then transferred to the bag or bottle. This process can be repeated if necessary to completely flush all medicament from container 10. After total transfer has been accomplished, container 10 including closure 18 which remain as a unit, normally is discarded.

The spike 30 separates from closure 18, however, and remains in the bag or bottle where it serves as an access post or dispensing spout.

Having fully described the invention, it is intended that it be limited solely by the lawful scope of the appended claims.

I claim:

1. The novel container and closure combination comprising:

a container having a cylindrical neck of reduced cross-section with respect to the main body of the container and terminating in an open end, said neck having a projection on its inner surface in proximity to said open end, and a closure for said open end having a skirt portion received in said open end and a shoulder at its outer end adapted to move into abutting relationship with the end of said cylindrical neck, said skirt portion having a cut out adapted for receiving said projection on the inner surface of said neck to hold said shoulder in non-abutting relationship with the end of said neck, said closure including a central fluid passage and a transverse fluid passage in communication therewith, the ends of said transverse fluid passage being sealed by the inner surface of said neck when said closure is held in the non-abutting position by the engagement of said projection in said cut out, said engagement being adapted to be overcome by force applied to the end of said closure whereby said shoulder is brought into abutting relationship with the end of said neck and the transverse passage is moved out of said neck and into fluid communication with the interior of said container, whereby a fluid pathway is provided from the interior of said container through said closure to the exterior.

2. The combination of claim 1 wherein the walls of said container are collapsible upon the application of squeezing force.

3. The combination of claim 1 wherein a spike having a sharpened outer end is carried by said central fluid passage of said closure and is adapted to be separated from said closure.

4. The combination of claim 3 wherein said outer end of said spike is covered by a protective cover.

5. The combination of claim 3 wherein said spike includes an airway.

6. The combination of claim 1, wherein the container contains a dry powdered medicament.

7. The combination of claim 6 wherein the medicament is thiopental sodium.

* * * * *